United States Patent [19]

Bundy

[11] Patent Number: 4,501,892
[45] Date of Patent: Feb. 26, 1985

[54] PYRIDYL BENZENEDIOLS

[75] Inventor: Gordon L. Bundy, Kalamazoo County, Mich.

[73] Assignee: The Upjohn Company, Kalamazoo, Mich.

[21] Appl. No.: 402,515

[22] Filed: Jul. 28, 1982

[51] Int. Cl.³ .................. C07D 405/04; C07D 405/06; C07D 405/12; A61K 31/335
[52] U.S. Cl. ..................................... 546/270; 548/336
[58] Field of Search ........................ 546/270; 548/336; 424/263, 273

[56] References Cited

FOREIGN PATENT DOCUMENTS 0069521 7/1981 European Pat. Off. ............ 546/270
0041652 12/1981 European Pat. Off. ............ 548/336

Primary Examiner—Henry R. Jiles
Assistant Examiner—J. G. Mullins
Attorney, Agent, or Firm—Lawrence T. Welch

[57] ABSTRACT

The present invention provides novel benzenediols and benzedioxins which selectively inhibit thromboxane $A_2$ synthetase and as such represent useful and potent pharmacological agents.

12 Claims, No Drawings

PYRIDYL BENZENEDIOLS

DESCRIPTION

BACKGROUND OF THE INVENTION

The present invention relates to novel compositions of matter. More particularly, the present invention relates to heteroaromatic substituted benzenediols and benzodioxins and derivatives thereof. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift 2,537,837.

SUMMARY OF THE INVENTION

Surprisingly and unexpectedly it has been found that selective thromboxane synthetase inhibition may be achieved by employing a compound of the formula I wherein $Z_1$ is
  (a) 4-pyridinyl,
  (b) 3-pyridinyl,
  (c) 3-pyridinyl substituted at the 4 position by
    (1) methyl,
    (2) —$OCH_3$,
    (3) —$N(CH_3)_2$, or
    (4) —$NH_2$, or
    (5) at the 2, 4, 5, or 6 position by chlorine;
  (d) imidazolyl, or
  (e) imidazolyl substituted by ($C_1$-$C_3$)alkyl;
wherein $X_1$ is
  (a) —$(CH_2)_n$—,
  (b) —O—,
  (c) —S—,
  (d) —S(O)—,
  (e) —$S(O)_2$—,
  (f) —$CH_2$—O—,
  (g) —$CH_2$—N($R_3$)—,
  (h) —N($R_3$)—$CH_2$—,
  (i) —CH(OH)—,
  (j) —C(O)—, or
  (k) —O—$CH_2$—;
with the proviso that when $X_1$ is (b), (c), (d), (e), (f), (g), (h), or (k), $Z_1$ is (a), (b), or (c), i.e., a pyridinyl substituent;
wherein $Q_1$ is
  (a) —CH(—$(CH_2)_m R_7$)—,
  (b) —C(O)—, or
  (c) —$CHR_5$—$CHR_6$—;
wherein $R_5$ and $R_6$ are different and are
  (a) hydrogen or
  (b) —$COOR_1$,
wherein $R_1$ is
  (a) hydrogen,
  (b) a pharmacologically acceptable cation,
  (c) ($C_1$-$C_{12}$)alkyl,
  (d) ($C_3$-$C_{10}$)cycloalkyl,
  (e) ($C_7$-$C_{12}$)aralkyl,
  (f) phenyl,
  (g) phenyl mono-, di, or trisubstituted by chloro, or ($C_1$-$C_3$)alkyl, or
  (h) phenyl para-substituted by
    (1) —NHCO—$R_{25}$,
    (2) —O—CO—$R_{26}$,
    (3) —CO—$R_{24}$,
    (4) —O—CO—(p—Ph)—$R_{27}$, or
    (5) —CH=N—NH—CO—$NH_2$,
wherein $R_{24}$ is phenyl or acetamidophenyl, $R_{25}$ is methyl, phenyl, acetamidophenyl, benazmidophenyl, or amino, $R_{26}$ is methyl, phenyl, amino or methoxy; and $R_{27}$ is hydrogen or acetamido, and wherein —(p—PH) is 1,4-phenylene;
wherein $R_3$ is
  (a) hydrogen, or
  (b) methyl;
wherein $R_7$ is
  (a) hydrogen,
  (b) —$CH_2OH$,
  (c) —$COOR_1$,
  (d) —$CH_2N(R_4)_2$,
  (e) —CN,
  (f) —$CON(R_4)_2$, or
  (g) —C(O)—$R_4$;
wherein m and n are the same or different and are the integers 0 to 4, inclusive;
including, pharmacologically acceptable acid addition salts thereof.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine,
4-ethylmorpholine,
1-isopropylpyrrolidine,
2-methylpyrrolidine,
1,4-dimethylpiperazine,
2-methylpiperidine, and the like, as well as amines containing water-solubilizing or hydrophilic groups, e.g., mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine, and the like. Further useful amine salts are the basic amino acid salts, e.g., lysine and
arginine.

Examples of suitable pharmacologically acceptable quaternary ammonium cations are tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art, e.g., as depicted in Example 8.

The compounds of the present invention will be named herein as benzenediols (when $Q_1$ is (a) or (b)) and benzodioxins (when $Q_1$ is (c)) using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2(TXA_2)$ was generated by mixing prostaglandin $H_2(PGH_2)$ with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, three compounds, dl-4-(3-pyridinylmethyl)-1,2-benzenediol, methyl glyoxylate acetal (Example 1) and an isomeric mixture of 2,3-dihydro-7 (and 6-) (3-pyridinylmethyl)-1,4-benzodioxin-2-carboxylic acid, sodium salt have been shown to be the most effective in inhibiting $TXA_2$ formation. The first compound has an approximate $ED_{50}$ in this system of 100 ng/ml, and the latter two compounds have an approximate $ED_{50}$ of between 10 and 100 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mp per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 500 μg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Charts A–K. In the charts, $n_1$ is an integer of from zero to 3, $R_{21}$ is hydrogen, methyl, or benzyl, and $R_{22}$ is $(C_1-C_3)$alkyl and all other variables are as defined above.

Chart A depicts a general scheme for the preparation of the compounds of the present invention. A compound of the formula A-1 is converted to the corresponding catechol (wherein $R_{21}$ is hydrogen) by means well known in the art and as described more fully in Preparations 1 and 2. (The preparation of these formula A-1 compounds is described below.) Alkylation of the formula A-1 diol with dichloracetic acid in the presence of potassium iodide and potassium carbonate in an alcoholic solvent yields the formula A-2 compound wherein m is zero, (see, e.g., Example 1). Alternatively, the compound wherein m is one is prepared by conjugate addition of the diol of formula A-1 to methyl propiolate as described in Example 3.

Treatment of the formula A-1 compound with a solution of phosgene in toluene gives the cyclic o-phenylene carbonate compound of the formula A-3. This is described more fully in Example 4.

Treatment of the formula A-1 catechol with ethyl 2,3-dibromopropionate and potassium carbonate in acetone yields the formula A-4 1,4-benzodioxane compound. This is described in Example 6.

Chart B depicts a method for preparing compounds of the present invention wherein $Z_1$ is imidazolyl or alkyl substituted imidazolyl. A compound of the formula B-1 (or the corresponding dimethoxyphenyl or dibenzyloxyphenyl compound) is converted to the corresponding chloroalkyl compound by sequential treatment with sodium borohydride, methanesulfonyl chloride and lithium chloride. The formula B-2 compound thus formed is then reacted with an imidazole or alkyl-substituted imidazole to yield the formula B-3 product.

Chart C depicts a general method for preparing compounds of the present invention wherein $Q_1$ is —CH(—$(CH_2)_m R_7$)—. A diol of the formula C-1 is condensed with an aldehyde of the formula CH(O)—$(CH_2)_m CO_2 R_{22}$ to yield the formula C-2 product.

Chart D depicts a general scheme for preparing compounds for the various values of n when $X_1$ is —$(CH_2)_n$—. A 3- or 4-substituted pyridine of the formula D-1 is brominated by means well known in the art. (Formula D-1 compounds are well known and readily available compounds.) The resultant formula D-2 compound is reacted with magnesium to yield the formula D-4 compound which is condensed with a formula D-4 aldehyde to yield the formula D-5 product. (Alternatively, the dimethoxy or dibenzyloxy compound corresponding to D-4 could be used.) This product may be hydrogenated (e.g., using a Parr apparatus and a palladium on carbon catalyst) to yield the formula D-6 product, or the formula D-7 product is prepared using mild oxidation (e.g., pyridinium chlorochromate, or potassium permanganate.)

Chart E depicts a method for preparing compounds of the present invention wherein $X_1$ is —O—. A 3- or 4-bromopyridine compound of the formula $E_1$ is condensed with a formula E-2 compound in the presence of potassium hydride in a solvent such as dimethylformamide (DMF) to yield the formula E-3 product.

Similarly, Chart F depicts a method for preparing compounds of the present invention when $X_1$ is —S—. A 3- or 4-bromopyridine compound is condensed with the formula F-2 thiol to yield the formula F-3 product. The preparation of F-2 is described in British Pat. No. 1,337,576. The compounds wherein $X_1$ is —S(O)— are prepared by mild oxidation of the F-3 compound, using, e.g., m-chloroperbenzoic acid. The compounds wherein $X_1$ is —$S(O)_2$— are prepared by a more vigorous oxidation of the F-3 compound. Phosphorous trichloride is then used to reduce the pyridine N-oxide which would be formed under these conditions.

Chart G depicts a method for preparing compounds of the present invention wherein $X_1$ is —$CH_2$—O—. A 3- or 4-substituted pyridine of the formula G-1 is condensed with the formula G-2 dimethoxyphenyl compound in the presence of potassium hydride in a solvent such as DMF to yield the formula G-3 product.

Chart H depicts a method for preparing compounds wherein $X_1$ is —$NHCH_2$—. A 3 or 4-aminopyridine of the formula H-1 is condensed with the formula H-2 compound to yield the formula H-3 intermediate which is converted to the compounds of the invention as described above.

Similarly, Charts I and J depict the preparation of the corresponding compounds wherein $X_1$ is —$OCH_2$— and —$CH_2$—NH—.

Chart K depicts a method for preparing chloropyridinyl compounds of this invention. The formula K-1 pyridinyl derivative is treated with m-chloroperbenzoic acid to yield the corresponding CVI N-oxide. The N-oxide of the formula K-2 is treated with phosphorous oxychloride to yield the corresponding chloropyridyl isomers of the formula K-3.

Compounds where $Z_1$ is 4-methylpyridine are prepared by converting the corresponding 4-chloropyridine of Chart K with methyl magnesium halides to the 4-methyl pyridine derivative according to the procedure described in K. Thomas and D. Jerchel, in "Newer Methods of Organic Chemistry," Vol. III., W. Foerst, ed., Academic Press, N.Y. 1964, pp. 74–75.

The 4-methoxy, 4-amino, and 4-N,N-dimethylamino derivatives are prepared from the corresponding 4-methoxh-3-bromopyridine (see T. Talik, Roczniki Chem., 36:1465 (1965)), 3-bromo-4-aminopyridine (see T. Talik, Roczniki Chem., 37:69 (1963)) and 3-bromo-4-dimethyslaminopyridine (see J. M. Essery and K. Schofield, J. Chem. Soc., 4953 (1960)), respectively, using the procedures described above.

Pharmacologically acceptable acid addition salts are prepared by methods well known in the art. The corresponding amides, phenacyl esters, and the like are also prepared by well known means, e.g., as depicted in U.S. Pat. Nos. 4,292,445 and 4,172,206. Free acids corresponding to the alkyl esters may be obtained by enzymatic hydrolysis using Plexaura homomalla-derived esterase. See, e.g., Schneider, et al., J. Am. Chem. Soc. 99:1222 (1977).

The remaining compounds within the scope of this invention are prepared by means well known in the art using readily available starting materials.

Certain compounds of the present invention are preferred. Thus, compounds of the formula I, wherein $X_1$ is —$(CH_2)_n$— (wherein n is zero or one, more preferably one), $Z_1$ is 3-pyridinyl, m is zero, $Q_1$ is —CH, —$(CH_2)_m R_7$)—, $R_1$ is $COOR_1$, and $R_1$ is —$CH_3$, Na, or H are preferred.

Thus, dl-4-(3-pyridinylmethyl)-1,2-benzendiol, methyl glyoxylate acetal and 2,3-dihydro-7-(and 6-)-(3-pyridinylmethyl)-1,4-benzedioxin-2-carboxylic acid, sodium salt are preferred compounds of this invention.

DESCRIPTION OF THE PREFERRED EMBODIMENTS

PREPARATION 1

3,4-Dibenzyloxyphenyl-(3-pyridyl)carbinol

Refer to Chart A (Formula A-1 compound wherein $R_{21}$ is benzyl). Following the general procedure of Sankey, et al., J. Heterocycl. Chem. 9:1049 (1972), a 1000 ml, 3-necked, round-bottomed flask is charged with 39.3 ml (63 mmoles) of 1.6M butyllithium in hexane. Anhydrous ether (100 ml) is added, the solution is cooled to −78°, and, with good stirring, a solution of 6.07 ml (9.954 g, 63 mmoles) of 3-bromopyridine in 100 ml of ether is added dropwise over 30 min. After 15 min at −78°, a solution of 20 g (63 mmoles) of 3,4-dibenzyloxybenzaldehyde in 100 ml of tetrahydrofuran and 100 ml of ether is added over 15 min. The mixture is stirred at −78° for 1 hr, then allowed to warm gradually to 25°. (Initially a pale yellow suspension, the reaction mixture becomes homogeneous at about 0°, and then begins precipitating a light tan solid by the time it reaches 25°). After 16 hr at 25°, the mixture is cooled to 0°, treated with 75 ml of 2M hydrochloric acid and shaken gently. The bottom two layers are saved (i.e., the neat amine hydrochloride and the acidic aqueous layer) and the organic layer is extracted with two additional 75 ml portions of 2M hydrochloric acid.

The neat (oily) hydrochloride salt and the combined acidic aqueous layer are made basic (pH 10-11) with ammonium hydroxide and extracted with three 200 ml portions of ether. The extracts are washed with brine, dried over anhydrous sodium sulfate, decolorized with Darco, filtered through Celite ® and concentrated in vacuo. The crude product, which crystallizes spontaneously, is triturated with 100 ml of 1:1 ether/hexane, filtered, washed with 2×10 ml of 1:1 ether/hexane, and dried under vacuum for 2 hr (0.01 mm, 25°). The crystalline product, pure carbinol weighed 16.5 g (66% of theory) and exhibited melting point of 87.5°-90.5° C. The mother liquors, 1.69 g, crystallize readily and still consist of mainly the desired product by TLC.

The IR ($\nu$max, mull) spectrum reveals peaks at 3177, 1595, 1507, 1461, 1455, 1427, 1379, 1342, 1266, 1225, 1136, 1067, 1035, 1025, 805, 741, 733, 693, and 603 cm$^{-1}$.

The NMR (CDCl$_3$; TMS, $\delta$) spectrum reveals peaks at 8.60-8.30, 7.90-6.70, 5.70, 5.12, and 5.06.

The mass spectrum reveals ions at m/e 397, 381, 320, 306, 290, 278, 262, 238, 172, 141, and 91.

The C:H:N ratio is 78.85:5.92:3.51.

PREPARATION 2

4-(3-Pyridinylmethyl)-1,2-benzenediol and the corresponding hydrochloride salt Refer to Chart A (preparation of the formula A-1 diol wherein R$_{21}$ is hydrogen).

Part A-HCl Salt.

A mixture of 43.0 g (108 mmoles) of dibenzyl ether (Preparation 1), 40 g of 10% palladium on carbon, 50 ml of 2.5M ethanolic hydrogen chloride and 1000 ml of ethanol is hydrogenated at about 30 psi hydrogen pressure on a Parr apparatus with a 2000 ml bottle. Hydrogen uptake essentially ceases after 4 hr, but shaking is continued overnight (22 hr total reaction time). The mixture is carefully filtered through Celite (argon atmosphere) and the catalyst is washed with additional ethanol. Removal of the ethanol from the combined filtrate in vacuo (bath temperature 35°) gives a semi-solid product, which upon trituration with ethyl acetate/ether, affors 22.0 g (86% of theory) of pure hydrochloride salt, melting point 150°-154°. The mother liquors (2.1 g) also crystallized readily and were essentially pure by TLC.

The IR ($\nu$max mull) spectrum reveals peaks at 3325, 3148, 1627, 1604, 1550, 1523, 1442, 1377, 1365, 1295, 1259, 1201, 1148, 1106, 1106, 878, 818, 750, 684, and 630 cm$^{-1}$.

The mass spectrum reveals ions at m/e 201.0798, 184, 172, 154, 144, 123, 105, 92, 77, 63, and 51.

The C:H:N:Cl ratio is 58.41:5.34:5.70:15.86.

Part B-Free amine.

A 4.0 g sample of the above hydrochloride salt is dissolved in 100 ml of water, the pH is adjusted to 7.5 with aqueous sodium carbonate, and the product is extracted with ethyl acetate. The extracts are washed with brine, dried over anhydrous sodium sulfate and evaporated. The crude crystalline product, 1.9 g is recrystallized from acetone and yields 1.54 g of titled compound with melting point of 150°-154° C. Since the recovery is low, the aqueous layers from the above extractions are fully saturated with sodium chloride and re-extracted with ethyl acetate. These extracts are dried and concentrated, affording 430 mg of additional compoun. (The pH of the aqueous layers following the second extraction is 7.20).

The IR ($\nu$max mull) spectrum reveals peaks at 3481, 3251, 2500, 1598, 1582, 1481, 1445, 1428, 1358, 1306, 1280, 1271, 1243, 1189, 1120, 1052, 966, 872, 803, 748, and 648 cm$^{-1}$.

The NMR (d$_6$ acetone; TMS, $\delta$) spectrum reveals peaks at 8.60-8.35, 7.75-7.45, 7.45-7.10, 6.95-6.05, and 3.85.

The mass spectrum reveals ions at m/e 201.0788 with a fragmentation pattern essentially identical to the hydrochloride salt above.

PREPARATION 3

3,4-Dimethoxyphenyl-(3-pyridinyl)carbinol

Refer to Chart A (Formula A-1 compound wherein Z$_1$ is 3-pyridinyl, X$_1$ is —CH(OH); and R$_{21}$ is CH$_3$).

A flame-dried, 1000 ml, three-necked round-bottomed flask fitted with a mechanical stirrer, 250 ml addition funnel and a nitrogen inlet is charged with 39.3 ml of 1.6M butyllithium in hexane. The butyllithium is diluted with 100 ml of anhydrous ether, cooled to $-78°$ and treated with a solution of 6.07 ml of 3-bromopyridine in 100 ml of ether added dropwise with good stirring under nitrogen over 30 min. Stirring is continued at $-78°$ for 15 min after completion of the bromopyridine addition. To the stirred, $-78°$ mixture is then added a soution of 10.46 g of 3,4-dimethoxy-benzaldehyde in 100 ml of ether. The reaction mixture is stirred at $-78°$ for 1 hr, $-50°$ for 1 hr, $-20°$ for 1 hr, then overnight at ambient temperature. The mixture is cooled to 0°, transferred to a separatory funnel and extracted with 3×75 ml of 2N hydrochloric acid. The aqueous layers are made basic (pH 10-11) by the addition of ammonium hydroxide and extracted with three 200 ml portions of ether. The extracts are washed with brine, dried over anhydrous sodium sulfate, decolorized with Darco and concentrted in vacuo.

The crude product (12.4 g) is chromatographed on a 600 g column of silica gel, packed with ethyl acetate and eluted with 4 l of ethyl acetate, 3 l of 1% triethylamine/ethylacetate and 4 l of 3% trimethylamine/ethyl acetate (50 ml fractions). Fractions 138-175 are clean by tlc and yield 5.8 g of pure titled carbinol which crystallizes on standing. Recrystallization of a portion of the product from ether give material with a mp of 100°-102° C.

The IR ($\nu$max mull) spectrum reveals peaks at 3062, 1591, 1580, 1515, 1455, 1441, 1417, 1377, 1345, 1270, 1229, 1183, 1155, 1137, 1055, 1027, 800, 772, 749, 724, 713, 675, and 635 cm$^{-1}$.

The NMR (CDCl$_3$, TMS, $\delta$) spectrum reveals peaks at 8.60-8.25, 7.80-7.60, 7.35-6.70, 5.75, 3.82, and and 3.78.

The mass spectrum reveals ions at m/e 245.1044; 229, 214, 186, 167, 154, 139, 123, and 106.

The C:H:N ratio is 68.05:6.13:5.67.

EXAMPLE 1 dl-4-(3-Pyridinylmethyl)-1,2-benzenediol, methyl glyoxylate acetal (Formula I, Z$_1$ is 3-pyridinyl, X$_1$ is —CH$_2$—, Q$_1$ is —CH(—(CH$_2$)$_m$R$_7$)—, m is zero, and R$_7$ is —COOCH$_3$)

Refer to Chart A (conversion of A-1 to A-2).

Following the general procedure of Grisar, et al., J. Med. Chem. 15(12):1273 (1972) a mixture of 100 mg of benzenediol of Preparation 2B (0.5 mmole), 276 mg (2 mmoles) of potassium carbonate, 17 mg (0.1 mmole) of potassium iodide, and 41 μl (0.5 mmole) of dichloroacetic acid in 10 ml of isopropyl alcohol is stirred vigorously while heating at reflux for 24 hr. The reaction mixture is cooled to 25° and one-half of the mixture is filtered (with great difficulty) through a medium-porosity sintered glass funnel. The resulting tan solids are dried and saved.

To the remaining one-half of the reaction mixture is added an additional 5 ml of isopropyl alcohol containing 20.5 μl of dichloroacetic acid (from a stock solution of 0.41 ml of dichloroacetic acid in 100 ml of isopropyl alcohol). The brown suspension is heated at reflux 48 hr longer, then cooled to 0°, treated with 8 drops of glacial acetic acid, followed by excess ethereal diazomethane. After 10 min at 0°, the mixture is poured into aqueous sodium bicarbonate and extracted with ethyl acetate. The extracts are washed with brine, dried over anhydrous sodium sulfate, and concentrated in vacuo. The crude product is chromatographed on a 10 g column of silica gel, packed and eluted (1 ml fractions) with ethyl acetate. Fractions 21–28 contained 24 mg of the clean acetal titled product as a colorless, viscous oil (36% of theory) homogeneous by TLC.

The IR ($\nu$max neat) spectrum reveals peaks at 1755, 1575, 1490, 1440, 1420, 1300, 1220, 1180, 1080, 1030, 1005, 960, 940, 810, 765, and 720 cm$^{-1}$.

The NMR (CDCl$_3$; TMS, $\delta$) spectrum reveals peaks at 8.6–8.4, 7.6–6.6, 6.34, 3.87, and 3.83.

The mass spectrum reveals ions at m/e 271.0838, 212, 182, 167, 154, 141, 128, 117, 102, 92, 77, 65, 51, and 39.

EXAMPLE 2 dl-4-(3-Pyridinylmethyl)-1,2-benzenediol, glyoxylic acid acetal, sodium salt (Formula I: $Z_1$ is 3-pyridinyl, $X_1$ is —CH$_2$—, $Q_1$ is —CH(—(CH$_2$)$_m$R$_7$)—, m is zero, and R$_7$ is —COONa; sodium salt of Example 1)

A solution of 18 mg (0.066 mmole), of the ester of Example 1 in 0.66 ml of methanol is treated with 0.66 ml of 1M aqueous sodium hydroxide and allowed to stand overnight at 25°. The water and methanol are then evaporated in a stream of nitrogen. The residue is triturated with 1 ml of acetone, filtered through a fine porosity sintered glass funnel, washed with 1 ml of cold acetone and dried in a vacuum dessicator (0.01 mm, 25°, 2 hr). The resulting off-white solid sodium salt (the titled product) weighs 17 mg and exhibits a melting point of 225°–230° C.

The IR ($\nu$max, microKBr) spectrum reveals peaks at 3425 (H$_2$O), 1641, 1497, 1445, 1427, 1315, 1248, 1195, 1111, and 1071 cm$^{-1}$.

The mass spectrum (after silylation) reveals ions at m/e 329.1077, 314, 286, 270, 258, 242, 212, 183, 167, and 154.

EXAMPLE 3

5-(3-Pyridinylmethyl)-1,3-benzodioxol-2-yl-acetic acid, methyl ester (Formula I: $Z_1$ is 3-pyridinyl, $X_1$ is —CH$_2$—, $Q_1$ is —CH(—(CH$_2$)$_m$R$_7$), m is one, and R$_7$ is —COOCH$_3$)

Refer to Chart A (conversion of A-1 (wherein R$_{21}$ is hydrogen) to A-2).

A solution of 500 mg of the diol of Preparation 2 and 10 ml of a 0.25M solution of methyl propiolate in tetrahydrofuran (1.11 ml of methyl propiolate diluted to exactlyu 50 ml with tetrahydrofuran) is stirred in an atmosphere of nitrogen for 5 days. By this time, TLC (20% acetone/methylene chloride) indicates four products less polar than starting material, with the least polar being the most abundant. The reaction mixture is poured into brine and extracted with ethyl acetate. The extracts are washed with water and dried, dried over anhydrous magnesium sulfate, and evaporated.

The crude product is chromatographed on a column containing 80 g of silica gel, packed with 15% acetone/methylene chloride and eluted (7 ml fractions) with 700 ml of 15% and 600 ml of 25% acetone-methylene chloride.

Fractions 65–79 are homogeneous by TLC and upon combination afford 100 mg (14% of theory) of titled acetal ester, a semi-viscous, colorless oil.

The IR ($\nu$max (neat)) spectrum reveals peaks at 1710, 1650, 1605, 1590, 1500, 1480, 1440, 1420, 1320, 1260, 1200, 1100, 1040, 1030, 950, 840, 820 and 720 cm$^{-1}$.

The NMR (CDCl$_3$; TMS, $\delta$) spectrum reveals peaks at 8.70–8.40, 7.80–6.80, 5.5, 4.00, and 3.80.

The mass spectrum reveals ions at m/e 285.1001, 252, 226, 212, 198, 182, 169, 154, 142, 127, 117, 92, 51, and 39.

TLC (silica gel GF) yields an R$_f$ of 0.28 (20% acetone/methylene chloride; starting material exhibited R$_f$ 0.10 on the same plate).

EXAMPLE 4

4-(3-Pyridinylmethyl)-1,2-benzenediol, cyclic carbonate (Formula I: $Z_1$ is 3-pyridinyl, $X_1$ is —CH$_2$—, and $Q_1$ is —C(O)—)

Refer to Chart A (conversion of A-1 wherein R$_{21}$ is hydrogen, to A-3).

A suspension of 201 mg (1.0 mmol) of the diol of Preparation 2B in 5 ml of methylene chloride is cooled to 0° and treated with 0.38 ml (2.18 mmol) of diisopropylethylamine followed by 2 ml of 12.5% phosgene in toluene. The reaction mixture is stirred at 0° for 1 hr and 25° for 1 hr, then poured into 1:1 brine/saturated aqueous sodium bicarbonate, and extracted with ethyl acetate. The extracts are washed with brine, dried over anhydrous sodium sulfate and evaporated, thereby affording 305 mg of crude product.

The crude product is chromatographed on a column containing 20 g of silica gel, packed with 10% acetone/methylene chloride and eluted (2–3 ml fractions) with 100 ml of 10% and 300 ml of 20% acetone/methylene chloride.

Fractions 92–141 are homogeneous by TLC and upon combination afford 80 mg of clean cyclic carbonate which crystallizes spontaneously. Trituration with ether followed by filtration and drying (0.1 mm, 25°, 18 hr) afford 36 mg of white crystals, mp 132°–134°.

The IR ($\nu$max (mull)) spectrum reveals peaks at 1762, 1607, 1594, 1455, 1445, 1367, 1292, 1268, 1254, 1208, and 1193 cm$^{-1}$.

The NMR (d$_6$-acetone; TMS, $\delta$) spectrum reveals peaks at 8.70–8.40, 7.75–6.60, and 3.93.

The mass spectrum reveals ions at m/e 227.0593, 197, 182, 172, 154, 143, 127, 105, 91, 77, 63, and 51.

TLC (silica gel GF) yields an R$_f$ of 0.57 (30% acetone/methylene chloride; the starting diol exhibited R$_f$ 0.32 on the same plate).

EXAMPLE 5

2,3-Dihydro-7-(and 6-)(3-pyridinylmethyl)-1,4-benzodioxin-2-carboxylic acid, ethyl ester (Formula I: $Z_1$ is 3-pyridinyl, $X_1$ is —$CH_2$—, $Q_1$ is —$CHR_5$—$CHR_6$—, and one of $R_5$ or $R_6$ is —$COOCH_2CH_3$, while the other is hydrogen)

Refer to Chart A (conversion of A-1 (wherein $R_{21}$ is hydrogen) to A-4).

To a solution of 402 mg (2 mmol) of the diol of Preparation 2 in 20 ml of deoxygenated (with nitrogen) acetone is added 360 mg of solid potassium carbonate, followed by 88 µl (157 mg, 0.6 mmol) of ethyl 2,3-dibromopropionate. The reaction mixture is then heated at reflux in a nitrogen atmosphere. At 2 hr, 4 hr and 6 hr, the reaction mixture is cooled, and an additional 220 mg of potassium carbonate and 88 µl of ethyl 2,3-dibromopropionate are added (each time). After an additional 18 hr at reflux, the mixture is cooled to room temperature and filtered through a medium-porosity sintered glass funnel. The solids are washed with fresh acetone, and the combined filtrate is concentrated in vacuo. The residue is diluted with water and extracted with ethyl acetate, and the extracts are subsequently washed with brine, dried over anhydrous sodium sulfate, and evaporated. The crude product (578 mg), essentially homogeneous and less polar than starting material by TLC, is chromatographed on a 20 g column of silica gel, packed and eluted with 15% acetone/methylene chloride (1×25 ml, then approximately 2 ml fractions).

Fractions 31-61 are homogeneous by TLC and are combinefd, thereby affording 445 mg (74% of theory) of clean titled ester a colorless, semi-viscous oil.

The IR ($\nu$max (neat)) spectrum reveals peaks at 1735, 1590, 1570, 1500, 1475, 1420, 1365, 1300, 1260, 1200, 1140, 1120, 1090, 1020, 800, 740 and 710 cm$^{-1}$.

The NMR (CDCl$_3$; TMS, $\delta$) spectrum reveals peaks at 8.60-8.40, 7.60-6.60, 4.85-4.70, 4.45-4.10, 3.86, and 1.24.

The mass spectrum reveals ions at m/e 299.1165, 226, 198, 170, 143, 142, 115, 92, and 43.

TLC (silica gel GF) yields an $R_f$ of 0.30 (60% ethyl acetate/hexane), 0.43 (15% acetone/methylene chloride), 0.35 (20% 2-propanol/hexane), and 0.40 (40% acetone/hexane).

Although this product appears completely homogeneous by TLC in the solvents listed, the $^{13}$C-NMR spectrum of this product contains additional peaks in the aromatic region indicating a mixture of the two possible positional isomers. Further support for this conclusion is the broad melting point range of the corresponding sodium salt (Example 6).

EXAMPLE 6

2,3-Dihydro-7-(and 6-)(3-pyridinylmethyl)-1,4-benzodioxin-2-carboxylic acid, sodium salt (Sodium salt of Example 5)

A solution of 230 mg (0.769 mmol) of the ester of Example 5 in 5 ml of methanol is treated with 7.69 ml of 0.10M aqueous sodium hydroxide, and the resulting clear solution is stirred at 25° for 64 hr (which is longer than necessary). The methanol and water are removed in vacuo and the residue is triturated with acetonitrile. When crystallization can not be induced, ether is added, but the salt still oils out rather than crystallizing. Trituration with acetone/ether finally leads to crystallization, and the solids are filtered and dried under vacuum (0.01 mm, 25°, 2 hr), thereby affording 178 mg of the sodium salt with a melting point of 145°-165° C., indicating a mixture of the two possible positional isomers.

EXAMPLE 7

Using the procedures of the preceding examples and the procedures depicted in Charts A–K, all of the remaining compounds within the scope of this invention are prepared.

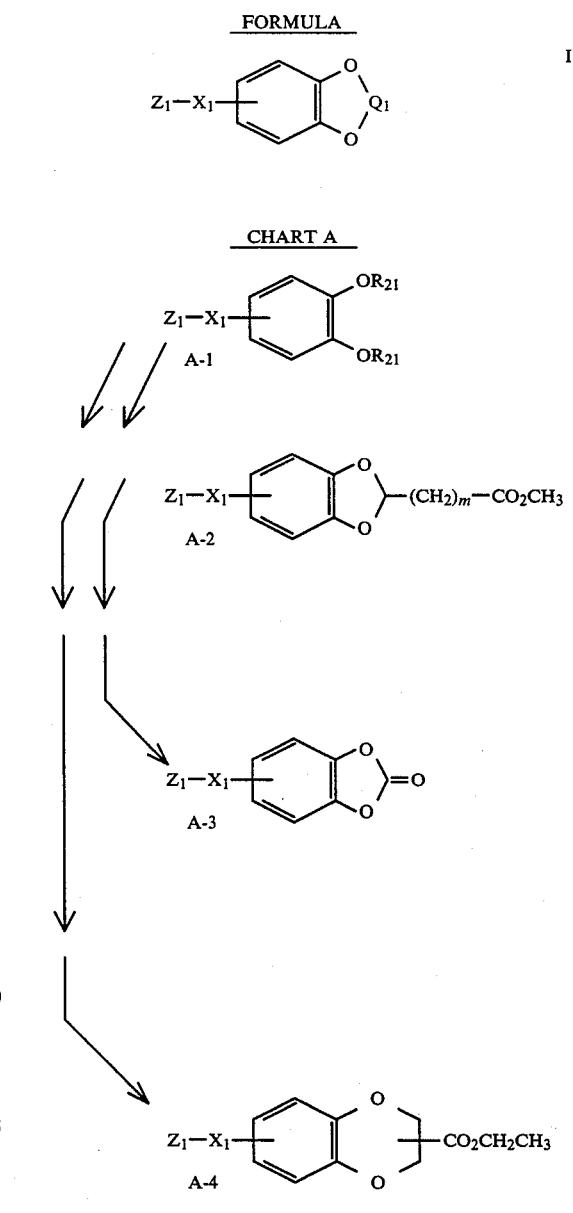

FORMULA I

CHART A

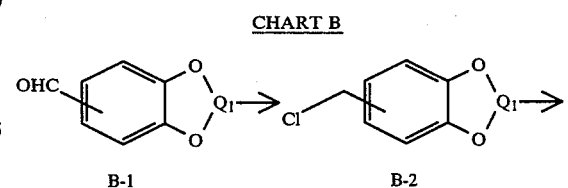

CHART B

-continued
CHART B
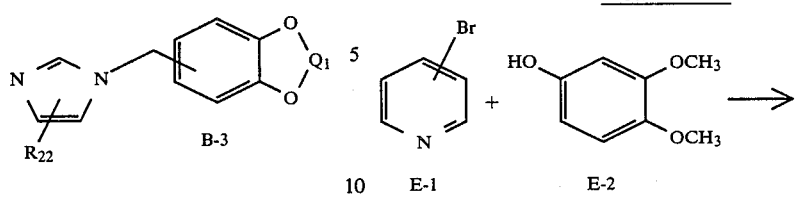
CHART C
CHART D
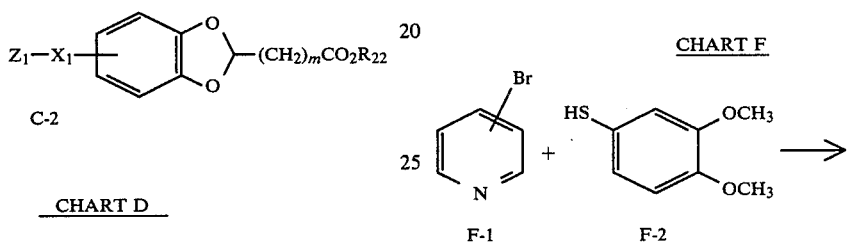
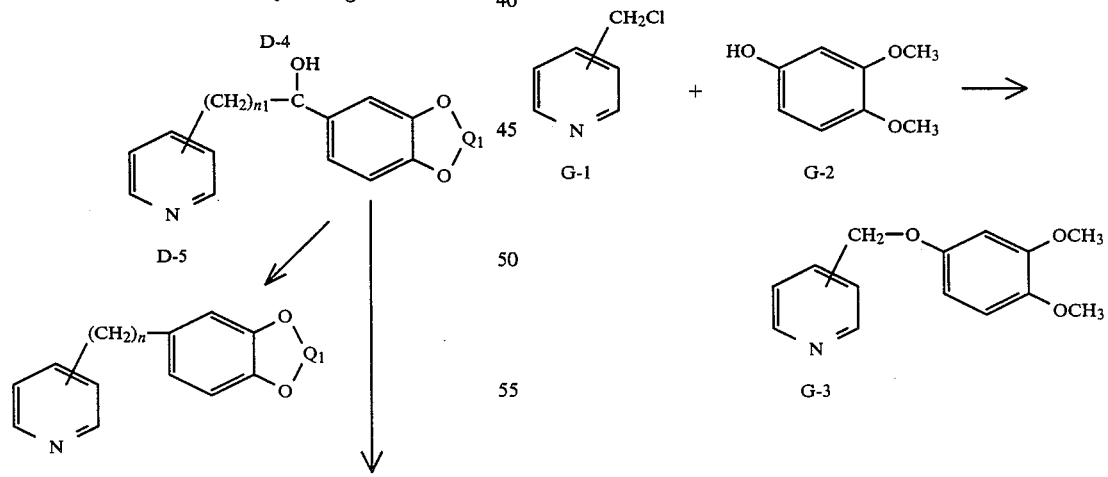
CHART E
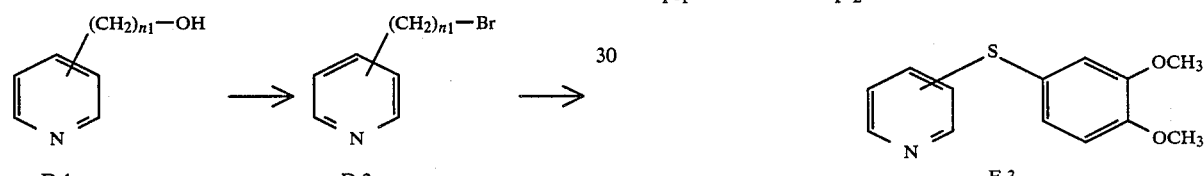
CHART F
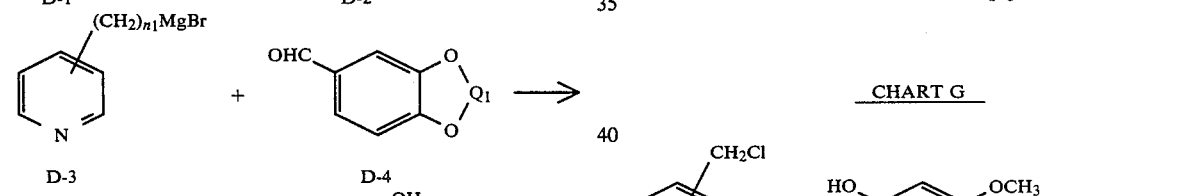
CHART G
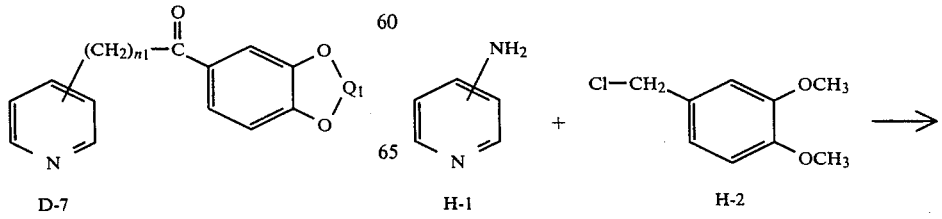
CHART H

CHART H -continued

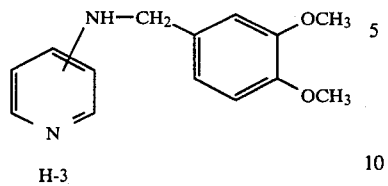

H-3

CHART I

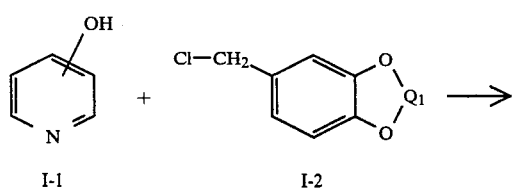

CHART J

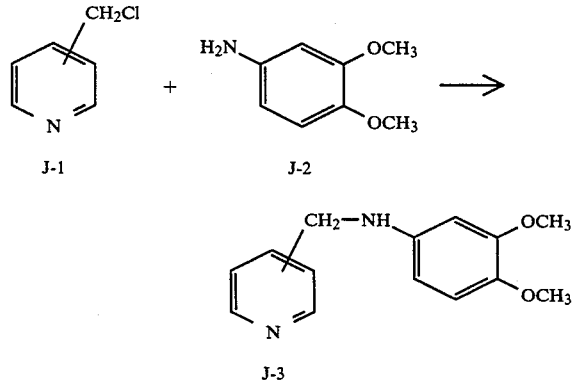

CHART K

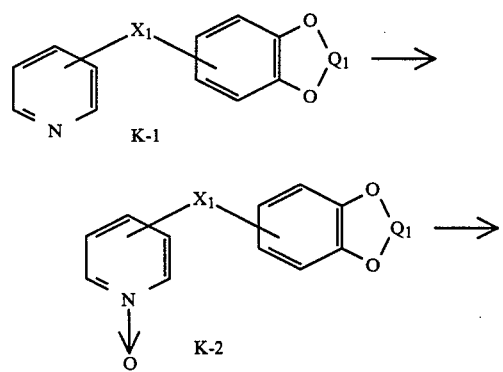

CHART K -continued

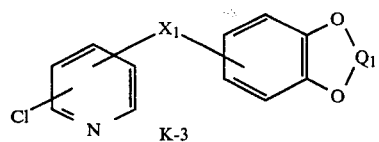

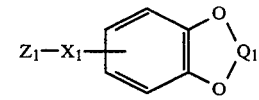

K-3

I claim:
1. A compound of the formula I

$$Z_1 - X_1 - \text{(benzodioxole-}Q_1\text{)}$$

I wherein $Z_1$ is
 (a) 4-pyridinyl,
 (b) 3-pyridinyl,
 (c) 3-pyridinyl substituted at the 4 position by
   (1) methyl,
   (2) —OCH$_3$,
   (3) —N(CH$_3$)$_2$, or
   (4) —NH$_2$, or
   (5) at the 2, 4, 5, or 6 position by chlorine;
 (d) imidazolyl, or
 (e) imidazolyl substituted by (C$_1$-C$_3$)alkyl;
wherein $X_1$ is
 (a) —(CH$_2$)$_n$—,
 (b) —O—,
 (c) —S—,
 (d) —S(O)—,
 (e) —S(O)$_2$—,
 (f) —CH$_2$—O—,
 (g) —CH$_2$—N(R$_3$)—,
 (h) —N(R$_3$)—CH$_2$—,
 (i) —CH(OH)—,
 (j) —C(O)—, or
 (k) —O—CH$_2$—;
with the proviso that when $X_1$ is —(CH$_2$)$_n$— and n is zero or when $X_1$ is (b), (c), (d), (e), (f), (g), (h), or (k), $Z_1$ is (a), (b), or (c), i.e., a pyridinyl substituent;
wherein $Q_1$ is
 (a) —CH(—(CH$_2$)$_m$R$_7$)—,
 (b) —C(O)—, or
 (c) —CHR$_5$—CHR$_6$—;
wherein R$_5$ and R$_6$ are different and are
 (a) hydrogen or
 (b) —COOR$_1$;
wherein R$_1$ is
 (a) hydrogen,
 (b) a pharmacologically acceptable cation, or
 (c) (C$_1$-C$_{12}$)alkyl;
wherein R$_3$ is
 (a) hydrogen, or
 (b) methyl;
wherein R$_7$ is
 (a) hydrogen,
 (b) —CH$_2$OH, or
 (c) —COOR$_1$;
wherein m and n are the same or different and are the integers 0 to 4, inclusive;
including, pharmacologically acceptable acid addition salts thereof.

2. A compound of claim 1, wherein $X_1$ is $-(CH_2)_n-$, n is zero or one, and $Z_1$ is 3-pyridinyl.

3. A compound of claim 2, wherein $Q_1$ is $-CH((CH_2)_mR_7)-$.

4. A compound of claim 2, wherein $Q_1$ $-C(O)-$.

5. A compound of claim 2, wherein $Q_1$ is $-CHR_5-CHR_6-$.

6. A compound of claim 3, wherein $R_7$ is $-COOR_1$.

7. dl-4-(3-Pyridinylmethyl)-1,2-benzenediol, methyl glyoxylate acetal, a compound of claim 6.

8. dl-4-(3-Pyridinylmethyl)-1,2-benzenediol, glyoxylic acid acetal, sodium salt, a compound of claim 6.

9. 5-(3-Pyridinylmethyl)-1,3-benzodioxol-2-yl-acetic acid, a compound of claim 6.

10. 4-(3-Pyridinylmethyl)-1,2-benzenediol, cyclic carbonate, a compound of claim 4.

11. 2,3-Dihydro-7-(and 6-)(3-pyridinylmethyl)-1,4-benzodioxin-2-carboxylic acid, ethyl ester, a compound of claim 5.

12. 2,3-Dihydro-7-(and 6-)(3-pyridinylmethyl)-1,4-benzodioxin-2-carboxylic acid, sodium salt, a compound of claim 5.

* * * * *